(12) United States Patent
Orbay et al.

(10) Patent No.: US 6,767,351 B2
(45) Date of Patent: Jul. 27, 2004

(54) FIXATION SYSTEM WITH MULTIDIRECTIONAL STABILIZATION PEGS

(75) Inventors: Jorge L. Orbay, Miami, FL (US); James Leone, Miami, FL (US); Dennis L. Steffen, Tavernier, FL (US)

(73) Assignee: Hand Innovations, Inc., Miami, FL (US)

( * ) Notice: Subject to any disclaimer, the term of this patent is extended or adjusted under 35 U.S.C. 154(b) by 0 days.

(21) Appl. No.: 10/159,612

(22) Filed: May 30, 2002

(65) Prior Publication Data

US 2002/0143338 A1 Oct. 3, 2002

Related U.S. Application Data

(63) Continuation-in-part of application No. 09/735,228, filed on Dec. 12, 2000, now Pat. No. 6,440,135, which is a continuation-in-part of application No. 09/524,058, filed on Mar. 13, 2000, now Pat. No. 6,364,882, and a continuation-in-part of application No. 09/495,854, filed on Feb. 1, 2000, now Pat. No. 6,358,250.

(51) Int. Cl.$^7$ ............................................. A61B 17/80
(52) U.S. Cl. ...................................................... 606/69
(58) Field of Search ............................. 606/66, 69, 72, 606/73, 60, 61, 70, 71

(56) References Cited

U.S. PATENT DOCUMENTS

| | | | |
|---|---|---|---|
| 472,913 A | 4/1892 | Taylor | |
| 2,500,370 A | 3/1950 | McKibbin | |
| 3,645,161 A | 2/1972 | Wesker | |
| 3,741,205 A | 6/1973 | Markolf et al. | |
| 4,484,570 A | 11/1984 | Sutter et al. | |
| 4,867,144 A | 9/1989 | Karas | |
| 5,006,120 A | 4/1991 | Carter | |
| 5,015,248 A | 5/1991 | Burstein et al. | |
| 5,304,180 A | 4/1994 | Slocum | |
| 5,437,667 A | 8/1995 | Papierski et al. | |
| 5,531,745 A | 7/1996 | Ray | |
| 5,607,426 A | 3/1997 | Ralph et al. | |
| 5,853,413 A | 12/1998 | Carter | |
| 5,879,350 A | 3/1999 | Sherman | |
| 5,968,047 A | 10/1999 | Reed | |
| 5,989,254 A | 11/1999 | Katz | |
| 6,010,503 A | 1/2000 | Richelsoph | |
| 6,022,350 A | 2/2000 | Ganem | |
| 6,053,917 A | 4/2000 | Sherman et al. | |
| 6,096,040 A | 8/2000 | Esser | |
| 6,197,028 B1 | 3/2001 | Ray et al. | |
| 6,221,073 B1 | 4/2001 | Weiss et al. | |
| 6,235,033 B1 | 5/2001 | Brace et al. | |
| 6,283,969 B1 | 9/2001 | Grusin et al. | |
| 6,290,703 B1 * | 9/2001 | Ganem | 606/73 |
| 6,322,562 B1 * | 11/2001 | Wolter | 606/69 |
| 6,527,775 B1 | 3/2003 | Warburton | |
| 6,595,993 B2 * | 7/2003 | Donno et al. | 606/71 |
| 6,602,255 B1 * | 8/2003 | Campbell et al. | 606/69 |
| 2002/0151899 A1 | 10/2002 | Bailey et al. | |
| 2003/0105461 A1 | 6/2003 | Putnam | |

OTHER PUBLICATIONS www.osteonics.com/osteonics/spine/xia2.html for XiaTM Spinal System for Polyaxial and Monoaxial Spinal Screws, 4 pages.

* cited by examiner

*Primary Examiner*—Kevin Shaver
*Assistant Examiner*—Michael B. Priddy
(74) *Attorney, Agent, or Firm*—Gordon & Jacobson, P.C.

(57) ABSTRACT

A fixation system includes a plate intended to be positioned against a bone, a plurality of bone screws for securing the plate along an non-fractured portion of the bone, and a plurality of bone pegs which extend from the plate and into bone fragments of the fracture to provide a supporting framework. The pegs can be oriented at various angles relative to an axis normal to the lower surface of the plate. For each peg, once the peg has been appropriately positioned within the peg hole, a set screw is threaded into the peg hole and tightened, thereby securing the peg in the selected orientation.

20 Claims, 8 Drawing Sheets

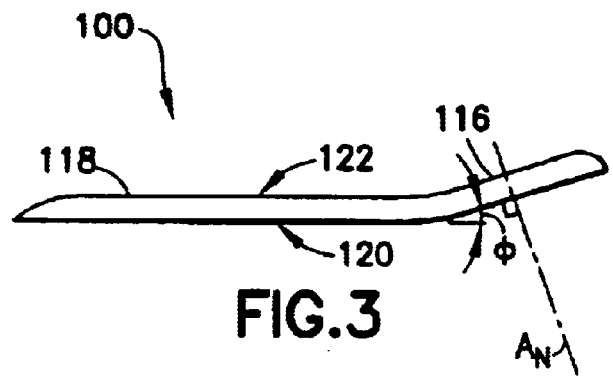
FIG.3
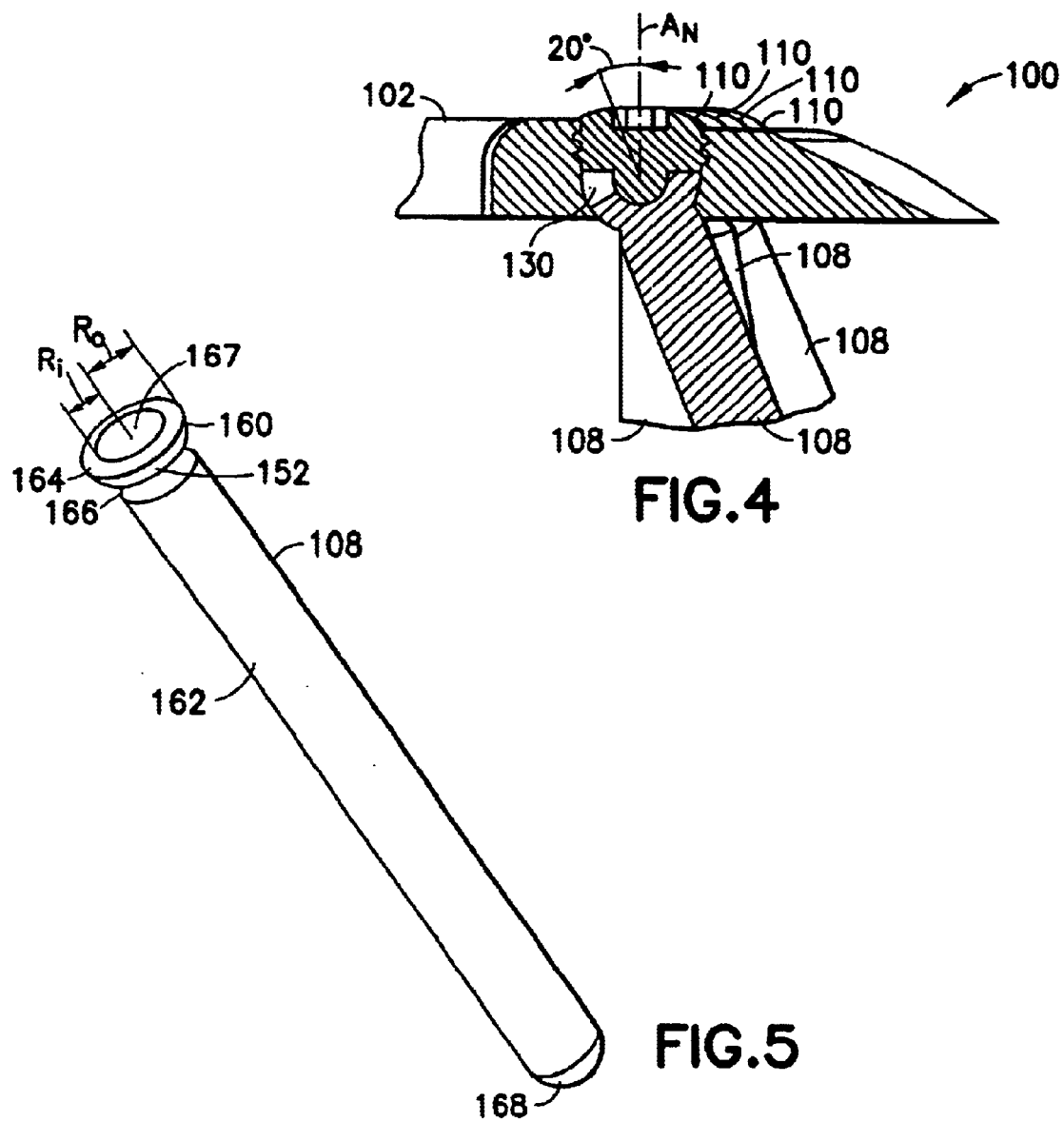
FIG.4
FIG.5

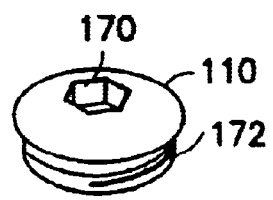
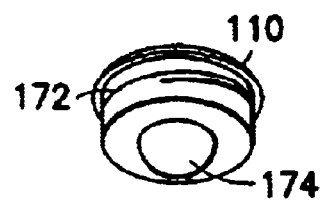
FIG.6
FIG.7
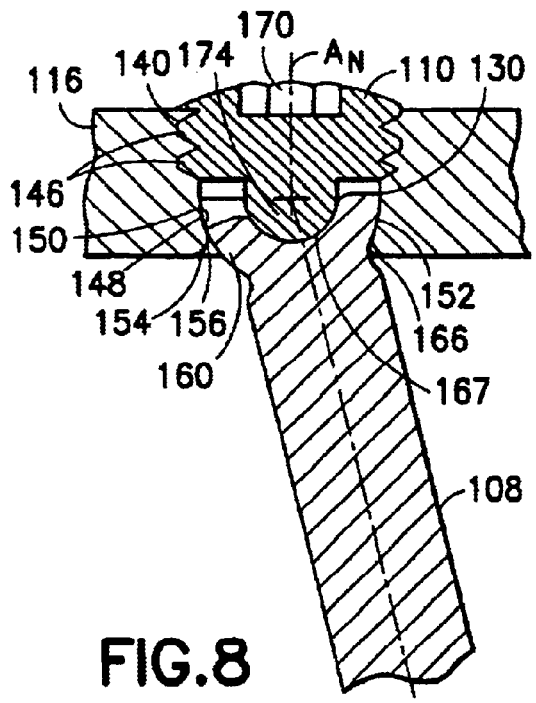
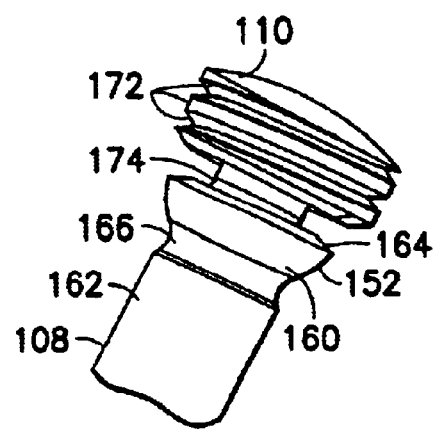
FIG.8
FIG.9

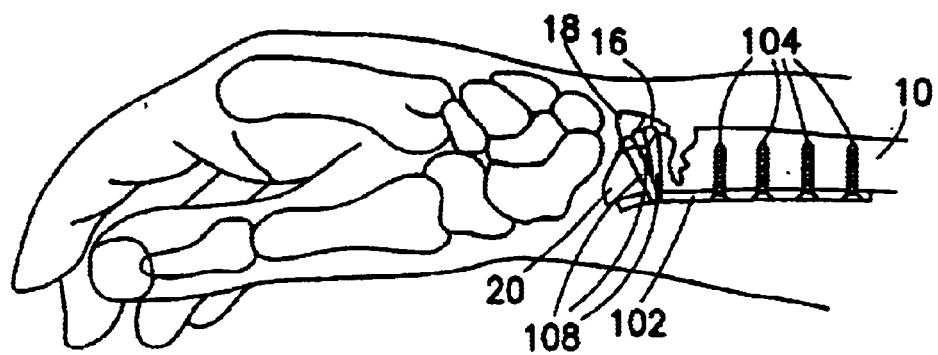
FIG.10
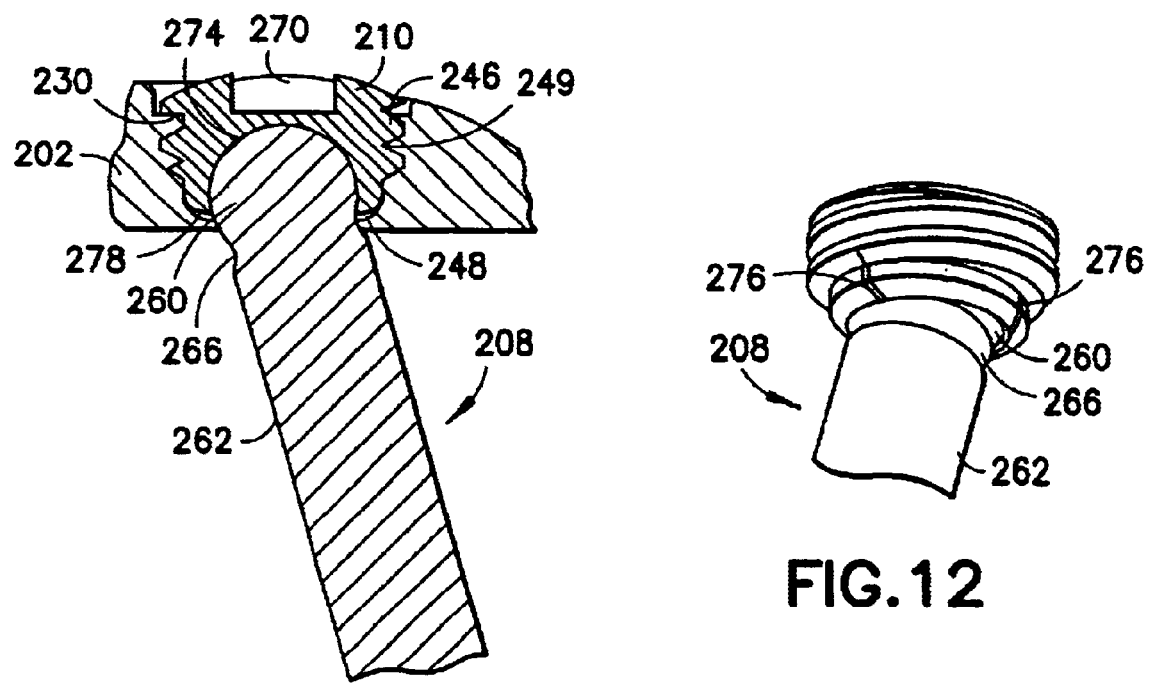
FIG.11
FIG.12

FIXATION SYSTEM WITH MULTIDIRECTIONAL STABILIZATION PEGS

This application is a continuation-in-part of U.S. Ser. No. 09/735,228, now U.S. Pat. No. 6,440,135 filed Dec. 12, 2000, which is a continuation-in-part now U.S. Pat. No. 6,364,882 of both U.S. Ser. No. 09/524,058, filed Mar. 13, 2000 and U.S. Ser. No. 09/495,854, now U.S. Pat. No. 6,358,250 filed Feb. 1, 2000, all of which are hereby incorporated by reference herein in their entireties.

BACKGROUND OF THE INVENTION

1. Field of the Invention

This invention relates broadly to surgical devices. More particularly, this invention relates to a bone fixation system having multidirectional bone fragment support pegs.

2. State of the Art

Referring to FIG. 1, a Colles' fracture is a fracture resulting from compressive forces being placed on the distal radius 10, and which causes backward displacement of the distal fragment 12 and radial deviation of the hand at the wrist 14. Often, a Colles' fracture will result in multiple bone fragments 16, 18, 20 which are movable and out of alignment relative to each other. If not properly treated, such fractures result in permanent wrist deformity. It is therefore important to align the fracture and fixate the bones relative to each other so that proper healing may occur.

Alignment and fixation are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time consuming procedure. Moreover, unless the bracing is quite complex, the fracture may not be properly stabilized. Plating utilizes a stabilizing metal plate typically against the dorsal side of the bones, and a set of parallel pins extending from the plate into the holes drilled in the bone fragments to provide stabilized fixation of the fragments. However, the currently available plate systems fail to provide desirable alignment and stabilization.

SUMMARY OF THE INVENTION

It is therefore an object of the invention to provide an improved fixation and alignment system for a Colles' fracture and other fractures.

It is another object of the invention to provide a fixation system which desirably aligns and stabilizes multiple bone fragments in a fracture to permit proper healing.

It is also an object of the invention to provide a fixation system which is highly adjustable to provide a customizable framework for bone fragment stabilization.

In accord with these objects, which will be discussed in detail below, a fracture fixation system is provided which generally includes a plate intended to be positioned against a non-fragmented proximal portion of a fractured bone, a plurality of bone screws for securing the plate along the non-fragmented portion of the bone, and a plurality of bone pegs coupled to the plate and extending therefrom into bone fragments adjacent the non-fragment portion.

According to a preferred embodiment of the invention, the plate is generally a T-shaped volar plate defining an elongate body, a head portion angled relative to the body, a first side which is intended to contact the bone, and a second side opposite the first side. The body portion includes a plurality of countersunk screw holes for the extension of the bone screws therethrough. The head portion includes a plurality of threaded peg holes for receiving the pegs therethrough. The pegs are angularly adjustable relative to the peg holes and can be independently fixed in selectable orientations; i.e., the pegs are multidirectional.

To stabilize a Colles' fracture, the volar plate is positioned with its first side against the volar side of the radius and bone screws are inserted through the bone screw holes into the radius to secure the volar plate to the radius. The bone fragments are then aligned and, through the peg holes, holes are drilled into and between the bone fragment at angles chosen by the surgeon. The pegs are then inserted into the peg holes and into the drilled holes, and a set screw (or screw cap) is inserted over each peg to lock the peg in the volar plate at the chosen orientation. The volar fixation system thereby stabilizes and secures the bone fragments in their proper orientation.

The various adjustably directable pegs can also be used in conjunction with fracture fixation plates adapted for fractures of other bones, e.g., the proximal and distal humerus, the proximal and distal ulna, the proximal and distal tibia, and the proximal and distal femur.

Additional objects and advantages of the invention will become apparent to those skilled in the art upon reference to the detailed description taken in conjunction with the provided figures.

BRIEF DESCRIPTION OF THE DRAWINGS

FIG. 3 is a side view of a volar plate according to the first embodiment of the volar fixation system of the invention;

FIG. 4 is a section view of the head portion of the volar fixation system according to the invention;

FIG. 5 is a proximal perspective view of a bone peg according to an embodiment of the invention;

FIGS. 6 and 7 are proximal and distal perspective views, respectively, of a set screw according to the a first embodiment of the invention;

FIG. 8 is a broken section view of a first embodiment of a directable peg assembly for a fracture fixation system according to the invention;

FIG. 9 is a broken perspective view of a peg and set screw according to the first embodiment of the directable peg assembly of the invention;

FIG. 10 is an illustration of the first embodiment of the volar fixation system provided in situ aligning and stabilizing a Colles' fracture;

FIG. 11 is a broken section view of a second embodiment of a directable peg assembly for a fracture fixation system according to the invention;

FIG. 12 is a broken perspective view of a peg and set screw according to the second embodiment of the directable peg assembly for a fracture fixation system according to the invention;

DETAILED DESCRIPTION OF THE PREFERRED EMBODIMENTS

Figure 1:
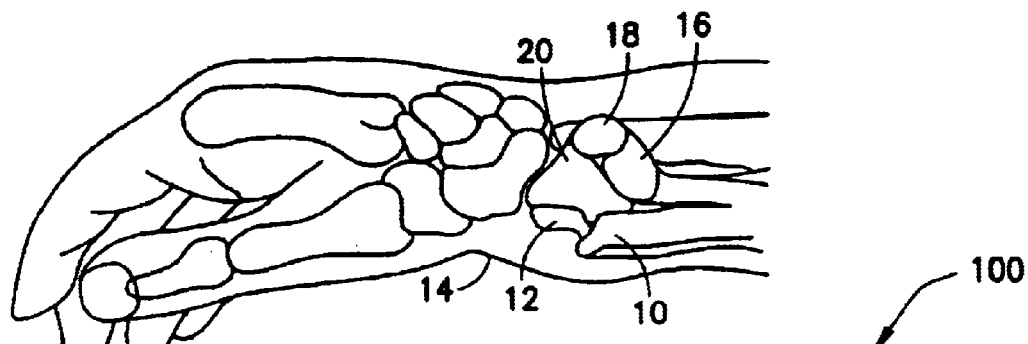
FIG. 1 is an illustration of an extremity subject to a Colles' fracture.
Figure 2:
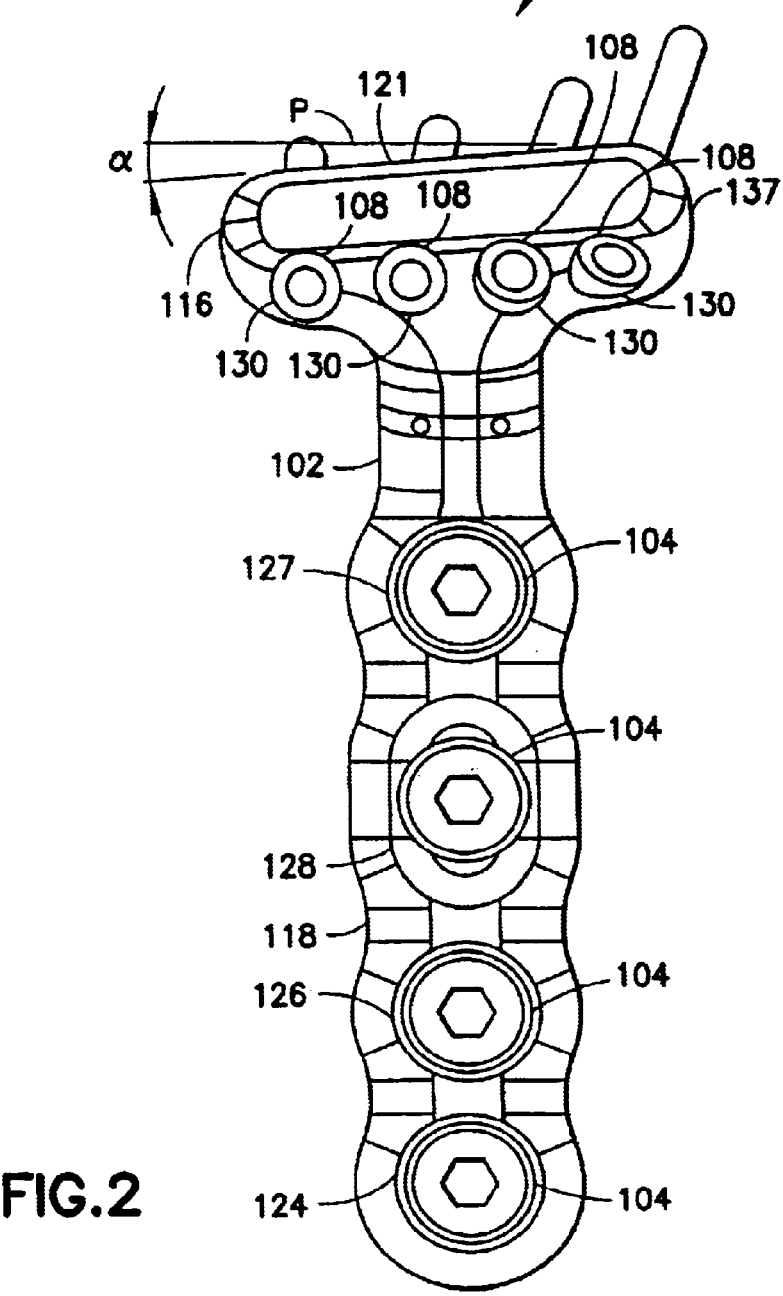
FIG. 2 is a top volar view of a right hand volar fixation system according to a first embodiment of the invention.

Turning now to FIGS. 2 through 4, a first embodiment of a fracture fixation system 100 is particularly adapted for aligning and stabilizing multiple bone fragments in a Colles' fracture. The system 100 generally includes a substantially rigid T-shaped plate 102 intended to be positioned against the volar side of the radial bone, a plurality of preferably self-tapping bone screws 104 for securing the plate 102 along a non-fractured portion of the radial bone, and a plurality of bone pegs 108 which extend from the plate 102 and into-bone fragments of a Colles' fracture.

The T-shaped plate 102 defines a head portion 116, an elongate body portion 118 angled relative to the head portion, a first side 120 which is intended to contact the bone, and a second side 122 opposite the first side. The first side 120 at the head portion is preferably planar, as is the first side at the body portion. As the head portion and body portion are angled relative to each other, the first side preferably defines two planar portions. The angle $\phi$ between the head portion 116 and the body portion 118 is preferably approximately 23° and bent at a radius of approximately 0.781 inch. The distal edge 121 of the head portion 116 is preferably angled proximally toward the medial side at an angle $\alpha$, e.g. 5°, relative to a line P, which is perpendicular to the body portion. The plate 102 preferably has a thickness of approximately 0.1 inch, and is preferably made from a titanium alloy, such as Ti-6A-4V.

The body portion 118 includes four preferably countersunk screw holes 124, 126, 127, 128 for the extension of the bone screws 104-therethrough. One of the screw holes, 128, is preferably generally elliptical (or oval).

The head portion 116 includes four peg holes 130, preferably closely spaced (e.g., within 0.25 inch of each other) and arranged along a line or a curve, for individually receiving the pegs 108 therethrough.

According to the invention, each peg can be directed through a range of angles within a respective peg hole and fixed at a desired angle within the range. Referring to FIGS. 4 and 8, according to a first embodiment of the invention, each peg hole 130 in the volar plate 102 includes a cylindrical upper bore 140 provided with threads 146 and a lower portion 148 having a radius of curvature. The lower end 154 of each peg hole includes a circumferential bevel 156.

Referring to FIGS. 4, 5 and 8, each peg 108 includes a head 160 and a cylindrical shaft 162. The proximal portion 164 of the head 160 includes a cup 167 having an outer radius $R_o$ substantially corresponding to the radius of the lower portion 148 of the peg holes 130, and a relatively smaller inner radius $R_i$ of curvature. The head 160 defines preferably approximately 160° of a sphere. The shaft 162 includes a slight taper 166 at the intersection with the head 160, and a rounded distal end 168. According to a preferred manufacture of the first embodiment, the cylindrical shaft 162 of each peg 108 is first provided with a sphere (not shown) or a hemisphere (not shown) at a proximal end. If a sphere is provided, it is cut to a hemisphere. The hemisphere is then hollowed and further reduced to the 160° shape. Finally, the taper 166 is provided at the intersection.

Referring to FIGS. 5 and 8, the surface 150 of the lower portion 148 of the peg hole 130 and/or the outer surface 152 of the head 160 of the peg 108 is preferably roughened, e.g., by electrical, mechanical, or chemical abrasion, or by the application of a coating or material having a high coefficient of friction.

Turning now to FIGS. 6 through 9, each set screw 110 includes a proximal hex socket 170, circumferential threads 172 adapted to engage the threads 146 of the upper bore 140 of the peg hole, and distal substantially hemispherical portion 174 having substantially the same radius of curvature as the inner radius of curvature $R_i$ of the cup 167, and preferably substantially smaller than a radius of the peg holes 130.

Referring to FIGS. 4 and 10, to stabilize a Colles' fracture, the plate 102 is positioned on the radius 10, and at least one hole is drilled through the elliptical screw hole on the volar plate and into the radius 10. Then, one or more bone screws 104 are inserted through the plate and into the bone. The fractured bones 16, 18, 20 are then adjusted under the plate 102 into their desired stabilized positions, and the bone screws 104 are tightened. Then, through the peg holes 130, the surgeon drills holes into the fracture location for the stabilization pegs 108. The holes may be drilled at any angle within a predefined range, and preferably at any angle within a range of 15° relative to an axis normal $A_N$ to the lower surface of the head of the volar plate. Each hole may be drilled at the same angle or at relatively different angles. After each hole is drilled, a peg 108 is inserted therein. Referring back to FIG. 8, the bevel 156 at the lower end 154 of the peg hole 130 and the taper 166 on the shaft cooperate to permit the peg to be oriented with greater freedom relative to the axis $A_N$, if required, as interference between the peg hole and peg shaft is thereby reduced. Once the peg 108 has been appropriately positioned within the peg hole, one of the set screws 110 is threaded into the upper bore 140 of the peg hole 130. The hemispherical portion 174 contacts the head 160 of the peg, seating in the concavity of the cup 167. As the set screw 110 is tightened, the surface 152 of the head of the peg, which may be roughened, is clamped between the set screw 110 and the roughened inner surface 150 of the lower portion of the peg hole 130, thereby securing the peg in the selected orientation. The other pegs are similarly positioned and angularly fixed.

Turning now to FIGS. 11 and 12, a second embodiment of a directable peg assembly for a fracture fixation plate is shown. The plate 202 includes threaded peg holes 230 that are generally larger in diameter than the head 260 of the pegs 208 intended for use therethrough. This permits a hole to be drilled through the peg hole 230 at a relatively greater angle than with respect to holes 130. The lower end 248 of the peg hole 230 is constricted relative to the upper threaded portion 249. The peg 208 includes a spherically-curved head 260, a cylindrical shaft 262, and an optionally constricted neck 266 therebetween. The set screw 210 includes a square opening 270 adapted to receive a square driver, threads 246 about its circumference, and a substantially spherically curved socket 274 adapted to receive the head 260 of the peg 208. As seen in FIG. 12, the lower portion of the set screw 210 includes expansion slots 276 which permit the lower portion of the set screw 210 to temporarily deform to receive the head 260 of the peg 208 (which has a diameter greater than the opening 278 of the spherical socket); i.e., the head 260 can be snapped into the socket 274.

In use, for each peg hole 230 and peg 208, holes are drilled through the peg holes and into the bone along axes at which it is desired to have pegs extend for stabilization of the fracture fragments. The head 260 of the peg 208 is snapped into the opening 278 of the socket 274. The shaft 262 of the peg 208 is then inserted into a respective bone hole until the set screw 210 meets the peg hole 230. It is appreciated that the set screw 210 can be rotated relative to the peg 208, as the socket 274 and spherical head 260 form a ball and socket coupling. As such, the set screw 210 is rotatably secured in the peg hole 230 to secure the peg 208 at the desired angle within the drilled hole.

Figure 13:
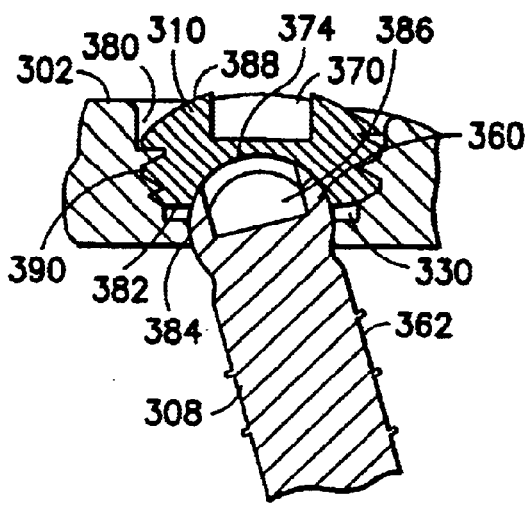
FIG. 13 is a broken section view of a third embodiment of a directable peg assembly for a fracture fixation system according to the invention.
Figure 14:
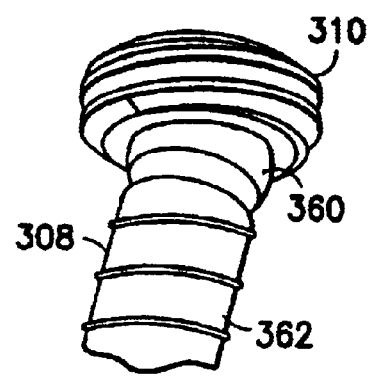
FIG. 14 is a broken perspective view of a peg and set screw according to the third embodiment of a directable peg assembly for a fracture fixation system according to the invention.

Turning now to FIGS. 13 and 14, a third embodiment of a directable peg assembly for a fracture fixation plate is shown. The plate 302 includes threaded peg holes 330 that preferably have a stepped diameter, with a relatively large countersink portion 380 adapted to receive the head of a set screw 310, a threaded central portion 382, and a relatively smaller lower portion 384. The peg 308 includes a substantially spherically-curved head 360 having a central square opening 386 adapted to receive a driver, and a threaded cylindrical shaft 362. The set screw 310 includes a head portion 388 having a square opening 370 for also receiving a driver, a threaded portion 390, and a lower spherically-curved socket 374.

In use, for each peg hole 330 and peg 308, a hole is drilled through a respective peg hole and into the bone at the angle at which it is desired to receive a peg for stabilization of the fracture. The peg 308 is then positioned within the peg hole 330 and rotatably driven into the bone with a driver (not shown). Once the peg 308 is fully seated against the lower portion 384 of the peg hole 330, the set screw 310 is threaded into the central portion 390 of the peg hole and urged against the head 360 of the peg 308 to clamp the peg in position. The head portion 388 of the set screw 310 preferably at least partially enters the countersink portion 380 of the peg hole to provide a lower profile to the assembly.

Figure 15:
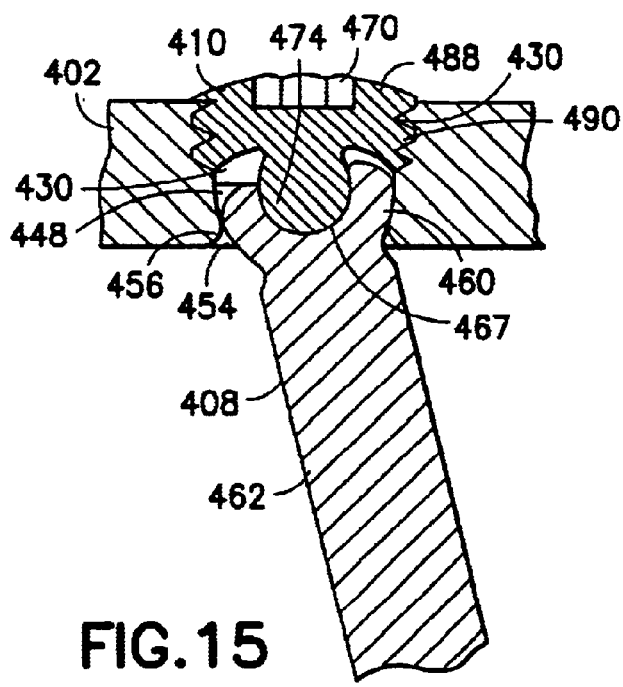
FIG. 15 is a broken section view of a fourth embodiment of a directable peg assembly for a fracture fixation system according to the invention.
Figure 16:
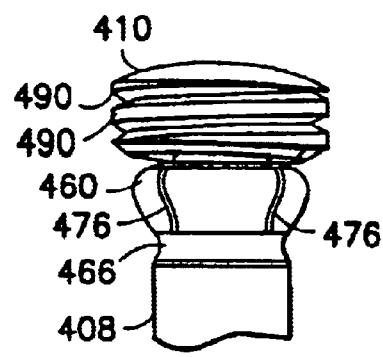
FIG. 16 is a broken perspective view of a peg and set screw according to the fourth embodiment of a directable peg assembly for a fracture fixation system according to the invention.

Turning now to FIGS. 15 and 16, a fourth embodiment of a directable peg assembly for a fracture fixation plate is shown. The plate 402 includes threaded peg holes 430 each with a lower portion 448 having a radius of curvature, and a lower end 454 provided with a preferably circumferential bevel 456. The peg 408 includes a spherically curved head 460 defining a socket 467 extending in excess of 180°, a cylindrical shaft 462, and an optionally tapered neck 466 therebetween. The head 460 about the socket 467 is provided with expansion slots 476. The set screw 410 includes an upper portion 488 having a square opening 470 for a driver, and threads 490, and a lower ball portion 474 adapted in size an curvature to snap into the socket 467.

In use, for each peg hole 430 and peg 408, holes are drilled through the peg hole and into the bone at the angles at which it is desired to receive pegs for stabilization of fragments of the fracture. The ball portion 474 of the set screw 410 is snapped into the socket 467, with the socket 467 able to expand to accept the ball portion 474 by provision of the expansion slots 476. The shaft 462 of the peg 408 is then inserted into a respective bone hole until the set screw 410 meets the peg hole 430. It is appreciated that the set screw 410 can rotate relative to the peg 408, as the ball portion 474 and socket 467 are rotatably coupled to each other. As such, the set screw 410 is then rotatably secured in the peg hole 430 to secure the peg 408 in the bone.

Figure 17:
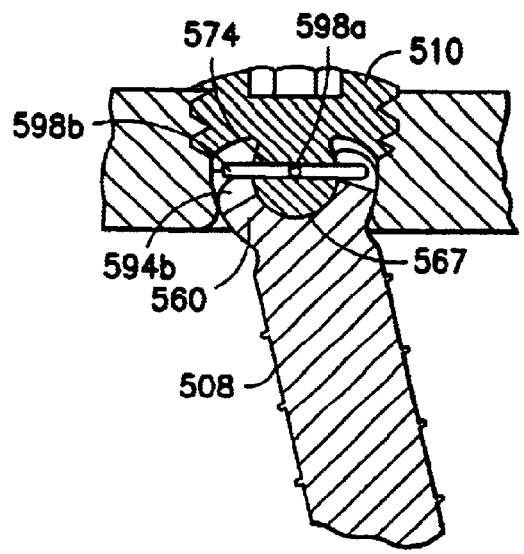
FIG. 17 is a broken section view of a fifth embodiment of a directable peg assembly for a fracture fixation system according to the invention.
Figure 18:
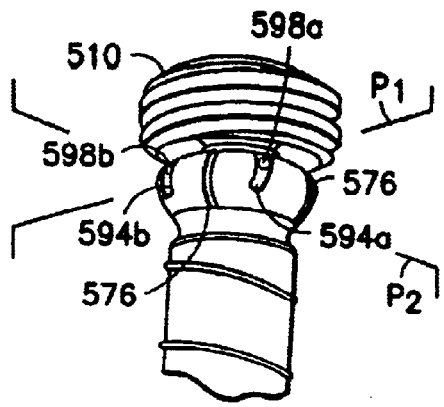
FIG. 18 is a broken perspective view of a peg and set screw according to the fifth embodiment of a directable peg assembly for a fracture fixation system according to the invention.

Turning now to FIGS. 17 and 18, a fifth embodiment of a directable peg assembly for a fracture fixation plate, substantially similar to the fourth embodiment, is shown. In the fifth embodiment, the head 560 of the peg 508 includes two sets of pin slots 594a, 594b defining two planes $P_1$ and $P_2$ oriented transverse to each other. In addition, the head 560 includes radial expansion slots 576. The ball portion 574 of the set screw 510 includes two pins 598a, 598b extending through a center thereof and oriented transverse to each other. The ball portion 574 is snapped into the socket 567 defined by the head 560 of the peg 508, and pins 598a, 598b are positioned through the pin slots 594a, 594b to rotatably lock the peg and set screw together, yet permit the peg 508 to articulate relative to the set screw 510. The fifth embodiment is suitable for rotatably inserting threaded pegs 508 into a bone hole via rotation of the set screw 510, and may be used in a similar manner to the fourth embodiment.

Figure 19:
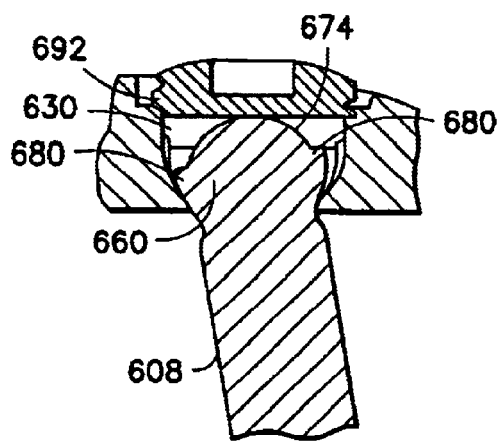
FIG. 19 is a broken section view of a sixth embodiment of a directable peg assembly for a fracture fixation system according to the invention.
Figure 20:
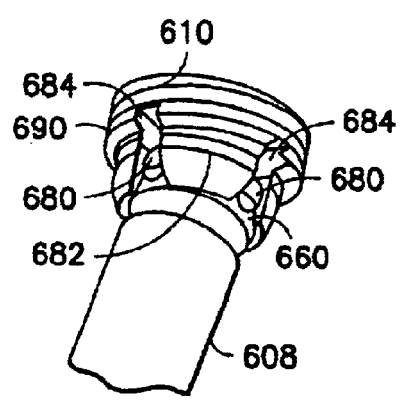
FIG. 20 is a broken perspective view of a peg and set screw according to the sixth embodiment of a directable peg assembly for a fracture fixation system according to the invention.

Turning now to FIGS. 19 and 20, a sixth embodiment of a directable peg assembly for a fracture fixation plate is shown. The assembly includes a peg 608 having a substantially spherically curved head 660 provided with four nubs 680 (two shown) arranged in 90° intervals about the periphery of the head 660. The set screw 610 includes lower walls 682 defining a socket 674 for the head 660. In addition, the walls 682 define slots 684 through which the nubs 680 can move.

In use, the assembly of the peg 608 with its set screw 610 functions substantially similar to a universal joint. The peg 608 is then inserted through a respective peg hole 630 and into a drilled hole in a bone until threads 690 on the set screw 610 engage mating threads 692 in the peg hole. The set screw 610 is then rotated, which causes rotation of the peg 608 within the drilled hole. When the set screw 610 is fully seated in the peg hole 630, the peg 608 is secured in the bone.

Figure 21:
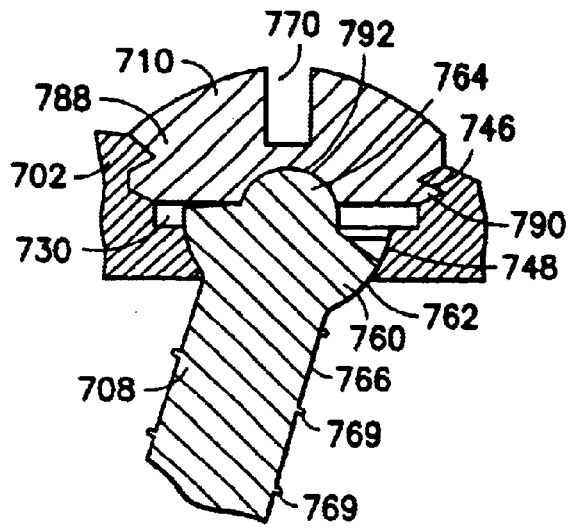
FIG. 21 is a broken section view of a seventh embodiment of directable peg assembly for a fracture fixation system according to the invention.
Figure 22:
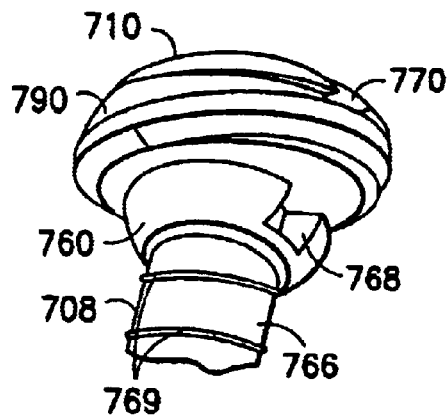
FIG. 22 is a broken perspective view of a peg and set screw according to the seventh embodiment of a directable peg assembly of the invention.

Turning now to FIGS. 21 and 22, a seventh embodiment of a directable peg assembly for a fracture fixation plate is shown. The peg holes 730 in the plate 702 each include a threaded cylindrical upper portion 746 and a spherically-curved lower portion 748 having a smaller hole diameter than the upper portion. Each peg 708 has a head 760 with a lower relatively larger spherically curved portion 762 and an upper relatively smaller spherically curved portion 764, and a shaft 766. The lower curved portion 762 preferably spherically curves through substantially 150°, while the upper curved portion 764 preferably spherically curves through substantially 210°. The peg shaft is optionally provided with threads 769, and when so provided, the lower curved portion 762 of the peg is provided with driver notches 768. The set screw 710 includes an upper portion 788 having a slot 770 or other structure for engagement by a driver, threads 790, and a lower socket 792.

In use, for each peg 708, a hole is drilled through a respective peg hole into the bone at an orientation desirable for receiving that particular peg for stabilization of the fracture. A peg 708 is then inserted through the peg hole 730 and into the drilled hole until the curved lower surface 762 of the head 760 of the peg seats against the curved lower portion 748 of the peg hole. If the peg has threads 769, a driver (not shown) may be coupled to the peg 708 at the notches 768 to rotationally drive the peg into the drilled hole. The set screw 710 is then threaded into the peg hole 730 until the socket 792 extends over the upper portion 764 of the head 760 of the peg and presses thereagainst to force the lower portion 762 of the head against spherically-curved lower portion 748 of the peg hole 730 to clamp the peg 708 in position. In the seventh embodiment, the socket 792 of the set screw 710 does not necessarily capture (i.e., extend more than 180° about) any portion of the head 760 of the peg 708. However, the socket 792 may be modified to enable such capture.

Figure 23:
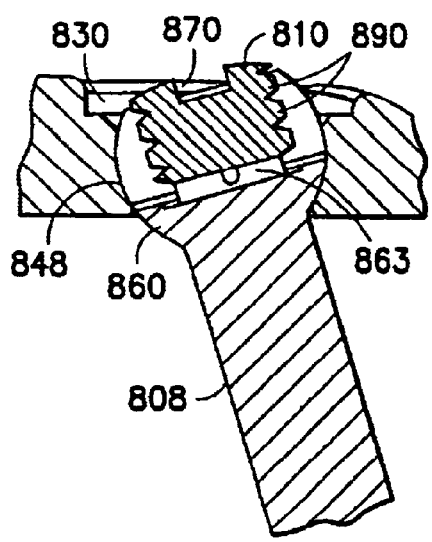
FIG. 23 is a broken section view of an eighth embodiment of directable peg assembly for a fracture fixation system according to the invention.
Figure 24:
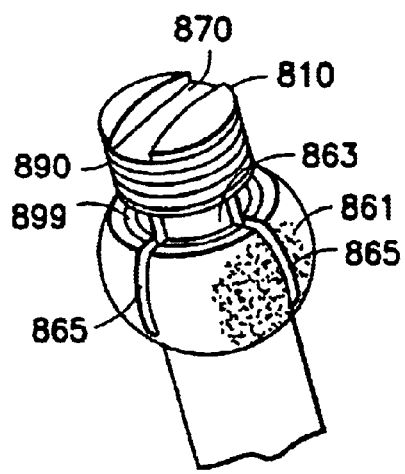
FIG. 24 is a broken exploded perspective view of a peg and set screw according to the eighth embodiment of a directable peg assembly of the invention.

Turning now to FIGS. 23 and 24, an eighth embodiment of a directable peg assembly for a fracture fixation plate is shown. The peg holes 830 of the plate each include a spherically-curved portion 848 preferably having a roughened relatively high friction surface. Each peg 808 has a substantially spherically-curved head 860 provided with a preferably roughened outer surface 861, an upper threaded axial bore 863, and a plurality of radial slots 865 extending between the outer surface and the bore. The set screw 810 includes an upper slot 870 for adapted to receive a driver and tapered threads 890.

In use, for each peg 808, a hole is drilled through a respective peg hole into the bone at an orientation desirable for receiving that particular peg for stabilization of the fracture. A peg 808 is then inserted through the peg hole 830 and into the drilled hole. When the peg 808 is fully seated in the peg hole 830 and at the desired angle, the set screw 810 in threadably inserted into the bore 863. The set screw 810 has a diameter slightly larger than the bore 863. As such, as the screw 810 is inserted, the head 860 of the peg 808 is enlarged at the slots 865 to accommodate the screw 810, and the high friction surfaces 861, 848 are forced against each other thereby locking the peg 808 in the peg hole 830 at its chosen axial orientation.

Figure 25:
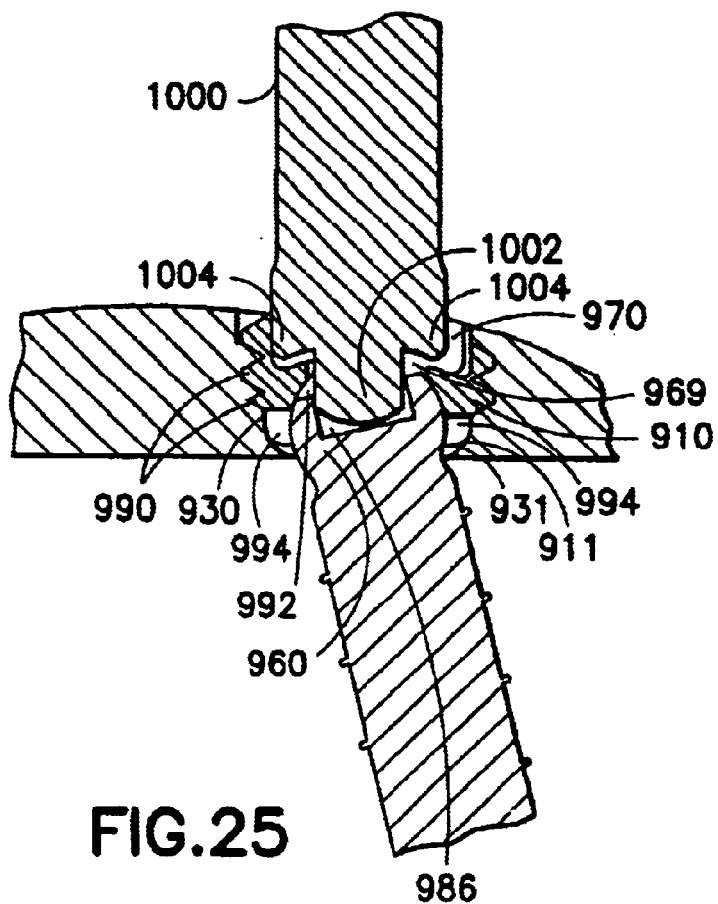
FIG. 25 is a broken section view of a ninth embodiment of directable peg assembly for a fracture fixation system according to the invention, shown with a driver for the peg.
Figure 26:
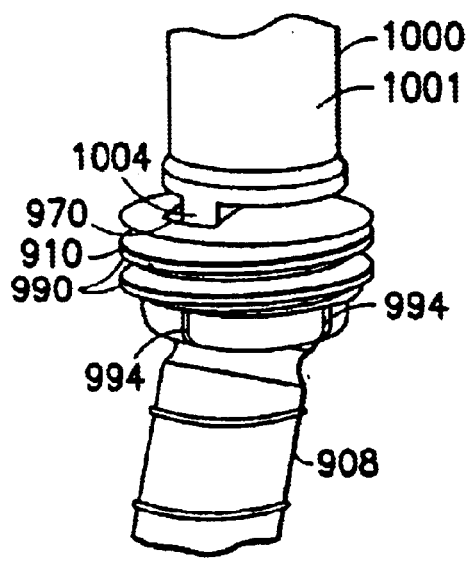
FIG. 26 is a broken perspective view of a peg, set screw and driver according to the ninth embodiment of a directable peg assembly of the invention.

Turning now to FIGS. 25 and 26, a ninth embodiment of a directable peg assembly for a fracture fixation plate is shown. The peg holes 930 and threaded pegs 908 are substantially similar to the peg holes 330 and pegs 308 of the third embodiment (FIGS. 13 and 14). It is noted that the lower end of the peg hole 930 has a lower curving taper 931. Also according to the ninth embodiment, the set screw 910 includes a central hole 969, an upper slot 970 extending across the hole 969, helical threads 990, a lower socket 992, and a plurality of compression slots 994 about the socket.

In use, for each peg 908, a hole is drilled through a respective peg hole 930 into the bone at an orientation desirable for receiving that particular peg for stabilization of the fracture. A driver 1000 having a shaft 1001 provided with a distalmost square end 1002 and relatively proximal flanges 1004 is then used for the assembly. The threaded peg 908 is positioned at the entry of the bone hole, and the set screw 910 is positioned thereover, with the socket 992 of the set screw resting on the head 960 of the peg. The square end 1002 of the driver is then inserted through the hole 969 and into a square opening 986 at the head 960 of the peg, and the flanges 1004 of the driver 1000 are inserted into the upper slot 970. The driver 1000 is rotated to threadably insert the peg 908 into the bone hole. When the set screw 910 meets the peg hole 930, it is also threaded therein with the driver, and when a lower portion 911 of the set screw contacts the curving taper 931 of the peg hole, the set screw is compressed about the compression slots 994 to secure the peg 908 in position.

There have been described and illustrated herein several embodiments of a volar fixation system, as well as directable peg systems suitable for numerous applications related to the fixation of various bone fractures. In each of the embodiments, the head of a peg is clamped between a portion of the fixation plate and a set screw, preferably with the head of the peg and fixation plate thereabout being treated to have, or having as material properties, high friction surfaces. While particular embodiments of the invention have been described, it is not intended that the invention be limited thereto, as it is intended that the invention be as broad in scope as the art will allow and that the specification be read likewise. Thus, while particular materials for the elements of the system have been disclosed, it will be appreciated that other materials may be used as well. In addition, fewer or more peg holes and bone pegs may be used, preferably such that at least two pegs angled in two dimensions relative to each other are provided. Also, while a right-handed volar plate is described with respect to an embodiment of the invention, it will be appreciated that right- or left-handed model, with such alternate models being mirror images of the models described. In addition, while it is disclosed that the pegs may be directed through a range of 15°, the peg holes and pegs may be modified to permit a greater, e.g. up to 30°, or smaller, e.g. 5°, range of such angular direction. Furthermore, while several drivers for applying rotational force to set screws and pegs have been disclosed, it will be appreciated that other rotational engagement means, e.g., a Phillips, slotted, star, multi-pin, or other configuration may be used. Also, the plate and pegs may be provided in different sizes adapted for implant into different size people. Furthermore, while four screw holes are described, it is understood that another number of screw holes may be provided in the plate, and that the screw holes may be located at positions other than shown. In addition, individual aspects from each of the embodiments may be combined with one or more aspects of the other embodiments. Moreover, while some elements have been described with respect to the mathematically defined shapes to which they correspond (e.g., spherical), it is appreciated that such elements need only correspond to such shapes within the tolerances required to permit the elements to adequately function together; i.e., the elements need only be "substantially" spherical in curvature. It will therefore be appreciated by those skilled in the art that yet other modifications could be made to the provided invention without deviating from its spirit and scope as claimed.

What is claimed is:

1. A fracture fixation system, comprising:
 a) a substantially rigid plate defining a body portion and a head portion angled relative to said body portion, said plate having a plurality of peg holes adapted to individually receive fixation pegs therein, said peg holes having an upper portion and a lower portion, said upper portion having a first internal thread, and said lower portion having a radius of curvature, and said plate including at least one non-threaded screw hole;
 b) a plurality of pegs each having a head and a shaft, said shaft sized to be received through said peg holes, and said head having a lower surface with substantially a same radius of curvature as said lower portion of said peg holes; and
 c) a plurality of set screws each having a body including a second thread rotationally engageable with said first thread, and a proximal rotational engagement means for permitting a rotational force to be applied to said set screw,
 wherein when said pegs are provided into respective peg holes, each said peg may be positioned at a plurality of angles relative to an axis normal to a lower surface of a portion of said fixation plate surrounding a respective peg hole, and once so positioned, respective set screws when threaded into said upper portions of said peg holes fix said pegs at their respective angles.

2. A fracture fixation system according to claim 1, wherein:
 said head portion defines said peg holes, and said body portion defines said at least one non-threaded screw hole.

3. A fracture fixation system, comprising:
 a) a substantially rigid plate defining a body portion and a head portion angled relative to said body portion, said plate having a plurality of peg holes adapted to individually receive fixation pegs therein, said peg holes having an upper portion and a lower portion, said upper portion having a first internal thread, and said lower portion having a surface with a radius of curvature and a relatively high coefficient of friction;
 b) a plurality of pegs each having a head and a shaft, said shaft sized to be received through said peg holes, and said head having a lower surface with substantially a same radius of curvature as said surface of said lower portion of said peg holes; and
 c) a plurality of set screws each having a body including a second thread rotationally engageable with said first thread, and a proximal rotational engagement means for permitting a rotational force to be applied to said set screw,
 wherein when said pegs are provided into respective peg holes, each said peg may be positioned at a plurality of angles relative to an axis normal to a lower surface of a portion of said fixation plate surrounding a respective peg hole, and once so positioned, respective set screws when threaded into said upper portions of said peg holes fix said pegs at their respective angles.

4. A fracture fixation system, comprising:
 a) a substantially rigid plate defining a body portion and a head portion angled relative to said body portion, said plate having a plurality of peg holes adapted to individually receive fixation pegs therein, said peg holes having an upper portion and a lower portion, said upper portion having a first internal thread, and said lower portion having a radius of curvature;
 b) a plurality of pegs each having a head and a shaft, said shaft sized to be received through said peg holes, and said head having a lower surface with substantially a same radius of curvature as said lower portion of said peg holes and also having a relatively high coefficient of friction; and
 c) a plurality of set screws each having a body including a second thread rotationally engageable with said first thread, and a proximal rotational engagement means for permitting a rotational force to be applied to said set screw,
 wherein when said pegs are provided into respective peg holes, each said peg may be positioned at a plurality of angles relative to an axis normal to a lower surface of a portion of said fixation plate surrounding a respective peg hole, and once so positioned, respective set screws when threaded into said upper portions of said peg holes fix said pegs at their respective angles.

5. A fracture fixation system, comprising:
 a) a substantially rigid plate defining a body portion and a head portion angled relative to said body portion and together configured in a T-shape, said plate having a plurality of peg holes adapted to individually receive fixation pegs therein, said peg holes having an upper portion and a lower portion, said upper portion having a first internal thread, and said lower portion having a radius of curvature;
 b) a plurality of pegs each having a head and a shaft, said shaft sized to be received through said peg holes, and said head having a lower surface with substantially a same radius of curvature as said lower portion of said peg holes; and
 c) a plurality of set screws each having a body including a second thread rotationally engageable with said first thread, and a proximal rotational engagement means for permitting a rotational force to be applied to said set screw,
 wherein when said pegs are provided into respective peg holes, each said peg may be positioned at a plurality of angles relative to an axis normal to a lower surface of a portion of said fixation plate surrounding a respective peg hole, and once so positioned, respective set screws when threaded into said upper portions of said peg holes fix said pegs at their respective angles.

6. A fracture fixation system according to claim 5, wherein:
 when said pegs are fixed at their respective angles, said pegs are adapted to provide a framework for supporting fractured bone fragments, said pegs of said framework defining a plurality of non-parallel axes.

7. A fracture fixation system according to claim 5, wherein:
 said peg holes are closely spaced in a linear or curvilinear arrangement.

8. A fracture fixation system according to claim 5, wherein:

said body portion includes at least one non-threaded screw hole.

9. A fracture fixation system according to claim 5, wherein:

said lower portion of said peg hole has a spherical radius of curvature.

10. A fracture fixation system according to claim 5, wherein:

said lower portion of each of said peg holes defines a surface having a relatively high coefficient of friction.

11. A fracture fixation system according to claim 5, wherein:

said lower surface of said head of each of said pegs has a surface having a relatively high coefficient of friction.

12. A fracture fixation system according to claim 5, wherein:

said plurality of angles is any angle within a predefined range of angles.

13. A fracture fixation system, comprising:

a) a substantially rigid plate defining a plurality of peg holes adapted to individually receive fixation pegs therein, said peg holes having a portion provided with a first internal thread;

b) a plurality of pegs each having a head portion and a shaft portion, said shaft portion sized to be received through said peg holes, and said head portion having an upper portion and a lower portion, said upper portion defining a ball portion with a first substantially spherical radius of curvature, said lower portion having a second substantially spherical radius of curvature larger than said first substantially spherical radius of curvature; and c) a plurality of set screws each having a body including a second thread rotationally engageable with said first thread, a proximal rotational engagement means for permitting a rotational force to be applied to said set screw, and a socket having said first substantially spherical radius of curvature such that each said set screw and its respective peg are adapted to articulate relative to each other by movement of said ball portion within said socket, wherein when said pegs are provided into respective peg holes, each said peg may be positioned at a plurality of angles relative to an axis normal to a lower surface of said plate, and once so positioned, respective set screws when threaded into said upper portions of said peg holes fix said pegs at their respective angles.

14. A fracture fixation system according to claim 13, wherein:

said peg holes have an upper portion provided with said first threads and a lower portion having a substantially spherical radius of curvature corresponding to said substantially spherical radius of curvature of said ball portion.

15. A fracture fixation system according to claim 13, wherein:

said ball portion curves through more than a hemisphere.

16. A fracture fixation system according to claim 15, wherein:

said ball portion curves through substantially 220°.

17. A fracture fixation system according to claim 13, wherein:

said lower portion is provided with engagement means for rotating said peg.

18. A fracture fixation system according to claim 13, wherein: said shaft of at least one of said pegs is threaded.

19. A fracture fixation system according to claim 13, wherein:

said plate includes a proximal body portion and a distal head portion angled relative to said body portion, and said head portion defines said peg holes.

20. A fracture fixation system according to claim 19, wherein:

said body portion includes at least one screw hole.

* * * * *